United States Patent [19]

Mangold et al.

[11] 4,410,733

[45] Oct. 18, 1983

[54] PREPARATION OF ACETALS OF MALONALDEHYDE

[75] Inventors: Dietrich Mangold, Neckargemuend; Josef Wahl, Schifferstadt; Wolf-Karlo Aders, Ellerstadt, all of Fed. Rep. of Germany

[73] Assignee: BASF Aktiengesellschaft, Ludwigshafen, Fed. Rep. of Germany

[21] Appl. No.: 337,487

[22] Filed: Jan. 6, 1982

[30] Foreign Application Priority Data

Feb. 21, 1981 [DE] Fed. Rep. of Germany ....... 3106576

[51] Int. Cl.$^3$ .............................................. C07C 41/54
[52] U.S. Cl. ...................,................ 568/603; 568/591; 568/592
[58] Field of Search .................. 568/591, 592, 603

[56] References Cited

FOREIGN PATENT DOCUMENTS 497280 11/1976 U.S.S.R. .............................. 568/603

OTHER PUBLICATIONS

Beilstein I, IV, p. 3635.
Van Alphen, "Ether and Ester", Rec. 49, pp. 492–500, esp. p. 499 (1930).
Houben–Weyl, vol. XIV/1, pp. 930–932.

*Primary Examiner*—Bernard Helfin
*Attorney, Agent, or Firm*—John H. Shurtleff

[57] ABSTRACT

Acetals of malonaldehyde are prepared by reacting an orthoester with a vinyl ether in the presence of a catalytic amount of FeCl$_3$. The malonaldehyde acetals obtainable by the process according to the invention are valuable intermediates in the preparation of dyes, crop protection agents and drugs.

9 Claims, No Drawings

PREPARATION OF ACETALS OF MALONALDEHYDE

The present invention relates to a novel process for the preparation of acetals of malonaldehyde by reacting an orthoester with a vinyl ether in the presence of a catalytic amount of $FeCl_3$.

Malonaldehyde acetals are preferably synthesized by catalyzed addition reaction of an orthoester with a vinyl ether, as described in a number of publication (Beilstein 1, IV, 3635).

The catalysts mentioned are boron fluoride and boron fluoride-etherate, in particular, as well as $AlCl_3$, $SnCl_2$, $HF$, $SO_2$ and $FeCl_3$. Results useful for preparative purposes are preferably obtained by using the highly corrosive and effluent-poisoning compounds $BF_3$ or $BF_3$-etherate.

These processes give malonaldehyde acetal yields of not more than 85% (cf. the use of $BF_3.Et_2O$ in U.S. Pat. No. 2,527,533, Example 1). Side reactions additionally occur, such as further addition reaction of the acetal formed with the vinyl ether, for example to give products of the pentaalkoxypentane type.

None of these publications mentions a highly undesirable side reaction:

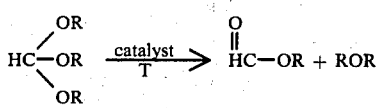

Fragmentation of the orthoesters into simple esters and dialkyl ethers is also known per se, from Rec. 49, (1930), 499. This paper shows that this decomposition and the ether formation especially take place when $FeCl_3$ is used as the catalyst.

This side reaction as a rule leads to drastic reductions in yield as a result of consumption of the relatively expensive orthoester component, and in particular to the formation of highly flammable ethers, which causes severe problems under industrial conditions. It is unambiguously depending on the amount of Lewis acid catalyst present.

The processes described are unsatisfactory with regard to economics and because of the formation of byproducts, and do not provide a safe, simple procedure.

We have found that acetals of malonaldehye of the formula

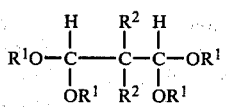

where the individual radicals $R^1$ and $R^2$ can be identical or different and each is an aliphatic, cycloaliphatic, araliphatic or aromatic radical, and $R^2$ can also be hydrogen, can be prepared in an advantageous manner if an orthoester of the formula

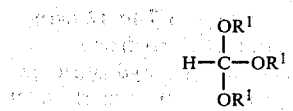

where $R^1$ has the above meanings, is reacted with a vinyl ether of the formula

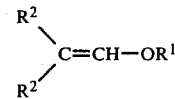

where $R^1$ and $R^2$ have the above meanings, in the presence of not more than 0.1 mole of iron(III) chloride per mole of starting material II, at from 0° to 70° C.

If trimethyl orthoformate and vinyl methyl ether are used, the reaction can be represented by the following equation:

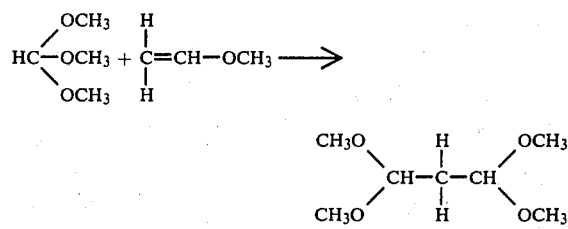

Compared with the conventional processes, the process according to the invention gives acetals of malonaldehyde by a simpler and more economical route and in a better yield and purity. The formation of by-products, for example of simple esters and ethers, is avoided to a far greater degree, and better overall results are thus achieved in respect of toxicity, reliable operation and saving of monitoring and control equipment. In the light of the prior art, all these results are surprising. It is also a substantial advantage of the present process that the favorable results are achieved with a greatly reduced amount of the expensive orthoester component.

Another advantage of the present process is that chemical deactivation of the catalyst is unnecessary and the reaction mixture can be worked up directly after the reaction, without further measures.

The starting materials II and III can be reacted in stoichiometric amounts or in an excess of II over III or III over II, from 1 to 3, in particular from 1 to 1.5, moles of starting material II advantageously being employed per mole of starting material III. Preferred starting materials II and III and accordingly preferred end products I are those in which the individual radicals $R^1$ and $R^2$ can be identical or different and each is alkyl of 1 to 12 carbon atoms, cycloalkyl of 5 to 8 carbon atoms, aralkyl or alkylaryl of 7 to 12 carbon atoms or phenyl, and $R^2$ can also be hydrogen. The above radicals can also be substituted by groups which are inert under the reaction conditions, eg. alkyl or alkoxy, each of 1 to 4 carbon atoms.

Examples of suitable starting materials II are trimethyl, triethyl, tripropyl, tributyl, triisobutyl, tri-sec.-butyl, tri-tert.-butyl, tripentyl, trihexyl, triheptyl, trioctyl, trinonyl, tridecyl, triundecyl, tridodecyl, triphenyl, methyl diethyl, methyl ethyl propyl, tricyclohexyl and tribenzyl orthoformate.

Suitable starting materials III include methyl, ethyl, propyl, isobutyl, cyclohexyl, isoamyl, neopentyl, 2-ethylhexan-1-yl, isopropyl, n-butyl, sec.-butyl, tert.-butyl, pentyl, hexyl, heptyl, nonyl, decyl, undecyl and dodecyl vinyl ether; and correspondingly substituted vinyl ethers in which the vinyl radical is monosubstituted or disubstituted by identical or different substituents from the group comprising methyl, ethyl, propyl, isopropyl, butyl, isobutyl, sec.-butyl, tert.-butyl, pentyl, hexyl, ethyl, octyl, cyclohexyl, benzyl and phenyl.

The reaction is carried out at from 0° to 70° C., advantageously at from 20° to 50° C., under atmospheric or superatmospheric pressure, continuously or batchwise. An organic solvent which is inert under the reaction conditions, eg. an aromatic hydrocarbon, can be used, but as a rule the starting materials II and III and the end product I serves as the reaction medium. Anhydrous or hydrated iron-III chloride can be used. Not more than 0.1, advantageously from 0.0001 to 0.1 and in particular from 0.0003 to 0.004, mole of the iron-III chloride catalyst is used per mole of starting material II.

The reaction can be carried out as follows: a mixture of the starting materials II and III and iron-III chloride is kept at the reaction temperature for from 0.25 to 10 hours. The end product is isolated in a conventional manner, for example by distillation. In the continuous preparation of the end product I, the catalyst can be adsorbed on a fixed carrier or can be introduced into the reactor, together with the reactants, as a solution in the orthoester or the reaction mixture.

The malonaldehyde acetals I which can be prepared by the process according to the invention are valuable intermediates in the preparation of dyes, crop protection agents and drugs. Regarding use of the products, reference may be made to the above publications.

In the Examples which follow, parts are by weight and bear the same relation to parts by volume as that of the kilogram to the liter.

EXAMPLE 1

65,000 parts of trimethyl orthoformate are introduced into a stirred vessel surmounted by a column, and 30 parts of anhydrous $FeCl_3$ are added. 28,000 parts of vinyl methyl ether are added at from 35° to 40° C., while stirring and cooling. Distillation of the excess orthoester is then started under atmospheric pressure (13,155 parts are recovered).

74,345 parts of 99% pure tetramethoxypropane of boiling point 58°-62° C./20 mbar are obtained by rectification under reduced pressure, corresponding to a yield of 92% (based on orthoester).

EXAMPLE 2

2 parts of anhydrous $FeCl_3$ are added to 592 parts of triethyl orthoformate in a stirred vessel, and 216 parts of ethyl vinyl ether are added at from 38° to 42° C.

133 parts of excess orthoester are then distilled off under reduced pressure (boiling point 45°-52° C./20 mbar). 607 parts of 98.5% pure tetraethoxypropane of boiling point 60°-62° C./0.2 mbar are obtained by rectification under reduced pressure, corresponding to a yield of 89% (based on orthoester).

EXAMPLE 3

In a manner similar to that in Example 1, 0.2 part of $FeCl_3$ is added to 392 parts of triethyl orthoformate, followed by 205 parts of propenyl ethyl ether. Distillation over a Vigreux column gives 37 parts of excess orthoester and 502 parts of 2-methyl-1,1,3,3-tetraethoxypropane of boiling point 88°-92° C./20 mbar, corresponding to a yield of 90% (based on orthoester).

EXAMPLE 4

112 parts/hour of a solution of 0.02 part of $FeCl_3$ in 100 parts of trimethyl orthoformate are introduced, via a metering pump, into a reaction tube which has a capacity of 100 parts by volume and is filled with glass beads, and at the same time 31.5 parts/hour of vinyl methyl ether are bubbled, via a control valve, into the bottom of the reactor in a manner such that no off-gas is obtained and complete vinyl ether conversion is ensured. The reaction temperature is 40° C.

The reaction product from 2 hours' operation is worked up in a manner similar to that in Example 1. As well as 114 parts of excess orthoester, 165 parts of 97% pure tetramethoxypropane of boiling point 58°-62° C./20 mbar are obtained, corresponding to a yield of 92% of theory (based on orthoester converted).

EXAMPLE 5

1,636 parts of trimethyl orthoformate containing 200 ppm of $FeCl_3$ are reacted with 320 parts of vinyl isobutyl ether at from 35° to 40° C. in a manner similar to that in Example 1.

Distillation recovers 292 parts of trimethylorthoformate and gives 607 parts of 1,1,3-trimethoxy-3-isobutoxypropane of boiling point 77°-83° C./20 mbar, as the end product I.

We claim:

1. A process for the preparation of an acetal of malonaldehyde of the formula

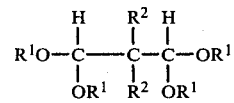

where the individual radicals $R^1$ and $R^2$ can be identical or different and each is an aliphatic, cycloaliphatic, araliphatic or aromatic radical, and $R^2$ can also be hydrogen, which process comprises:

reacting

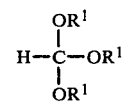

where $R^1$ has the above meanings, with a vinyl ether of the formula

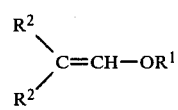

where $R^1$ and $R^2$ have the above meanings, in an excess of II over III and in the presence of a catalytic amount of not more than 0.004 mole of $FeCl_3$ per mole of starting material II, at a temperature of from 0° to 70° C., and isolating the end product I from the reaction mixture.

2. A process as claimed in claim 1 wherein $R^1$ and $R^2$ of the starting materials II and III are identical or different and each is a radical selected from the group consisting of alkyl of 1 to 12 carbon atoms, cycloalkyl of 5 to 8 carbon atoms, aralkyl or alkylaryl of 7 to 12 carbon atoms, and phenyl, and $R^2$ can also be hydrogen, with the proviso that each radical other than hydrogen may be further substituted by a group which is inert under the reaction conditions.

3. A process as claimed in claim 2 wherein the inert group is alkyl or alkoxy of 1 to 4 carbon atoms.

4. A process as claimed in claim 3 wherein the reaction is carried out with from 0.0001 to 0.004 mole of FeCl$_3$ per mole of starting material.

5. A process as claimed in claim 1 wherein the reaction mixture is worked up directly after the reaction without chemical deactivation of the FeCl$_3$ catalyst when isolating the end product I.

6. A process as claimed in claim 3 wherein the reaction mixture is worked up directly after the reaction without chemical deactivation of the FeCl$_3$ catalyst when isolating the end product I.

7. A process as claimed in claim 1, wherein the reaction is carried out with an excess of up to 3 moles of starting material II per mmole of starting material III.

8. A process as claimed in claim 1, wherein the reaction is carried out at from 20° to 50° C.

9. A process as claimed in claim 1, wherein the reaction is carried out with from 0.0001 to 0.004 mole of FeCl$_3$ per mole of starting material II.

* * * * *